United States Patent [19]

Abatjoglou et al.

[11] Patent Number: 5,114,473

[45] Date of Patent: May 19, 1992

[54] TRANSITION METAL RECOVERY

[75] Inventors: Anthony G. Abatjoglou, Charleston; David R. Bryant, South Charleston, both of W. Va.

[73] Assignee: Union Carbide Chemicals and Plastics Technology Corporation, Danbury, Conn.

[21] Appl. No.: 236,221

[22] Filed: Aug. 25, 1988

[51] Int. Cl.⁵ .............................. C01G 55/00
[52] U.S. Cl. ......................... 75/722; 423/22
[58] Field of Search .................. 75/722; 423/22

[56] References Cited

U.S. PATENT DOCUMENTS

| | | | |
|---|---|---|---|
| 3,954,883 | 5/1976 | Haag et al. | 260/614 A |
| 4,012,481 | 3/1977 | Baltz | 75/722 |
| 4,111,856 | 9/1978 | Haag et al. | 521/30 |
| 4,145,486 | 3/1979 | Haag et al. | 521/31 |
| 4,242,284 | 12/1980 | Harris et al. | 568/454 |
| 4,248,802 | 2/1981 | Kuntz | 568/454 |
| 4,292,196 | 9/1981 | Homeier et al. | 252/412 |
| 4,292,452 | 9/1981 | Lee et al. | 568/881 |
| 4,364,907 | 12/1982 | Barnes | 423/22 |
| 4,435,575 | 3/1984 | Cainelli et al. | 546/341 |
| 4,504,588 | 3/1985 | Gartner et al. | 502/24 |
| 4,565,799 | 1/1986 | Giordano, Jr. et al. | 502/155 |
| 4,606,326 | 8/1986 | Giordano, Jr. et al. | 126/400 |
| 4,633,021 | 12/1986 | Hanes | 568/454 |
| 4,717,785 | 1/1988 | Paxson | 585/823 |

FOREIGN PATENT DOCUMENTS

| | | |
|---|---|---|
| 147824 | of 0000 | European Pat. Off. . |
| 0224209 | 6/1987 | European Pat. Off. . |
| 3411034 | 9/1985 | Fed. Rep. of Germany . |
| 3443474 | 5/1986 | Fed. Rep. of Germany . |
| 1330644 | 9/1973 | United Kingdom . |

OTHER PUBLICATIONS

Chemical Abstracts, vol. 98, No. 6, Abstract No. 41336f, Smith et al., "Rhodium Complexes . . . ".

T. J. Rabek, "Basic Theory of Synthesis of Poly-Electrolites and Ion-Exchange Resins", Publisher PWN, Warzaw, 1960, pp. 423–426.

*Primary Examiner*—Peter D. Rosenberg
*Attorney, Agent, or Firm*—Reynold J. Finnegan

[57] ABSTRACT

A method for recovering a transition metal such as rhodium from a polar or non-polar liquid by contacting said transition metal-containing liquid with an ion-exchange resin having bonded ionically thereto an organophosphorus ligand; the transition metal can be eluted from the bed using a liquid containing a sufficient concentration of organophosphorus ligand.

17 Claims, 1 Drawing Sheet

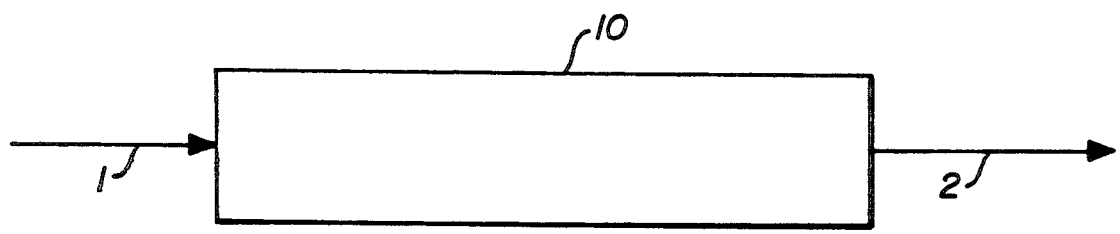

TRANSITION METAL RECOVERY

BACKGROUND OF THE INVENTION

1. Field of the Invention

This invention broadly relates to a method useful for recovering a Group VIII transition metal from a liquid, and in particular from liquids containing the transition metal in solution at a low concentration. This invention particularly relates to a method for recovering rhodium from its liquid solutions, such as from the aldehyde product of an olefin hydroformylation process.

2. Description of Related Art

Processes using homogeneous transition metal catalysts such as rhodium are well-known. For example, transition metal catalysts are used in processes for hydrogenating unsaturated compounds, such as copolymers of a conjugated diene and co-polymerizable monomers as described in U.S. Pat. Nos. 4,464,515 and 4,503,196, for carbonylating methanol to acetic acid, for oligomerizing olefins, for hydrocyanating butadiene to adiponitrile, for decarbonylating aldehydes and for hydrosilylating olefins. Particularly illustrative of such homogeneous catalysis systems is the catalytic hydroformylation of olefinic compounds with carbon monoxide and hydrogen to produce aldehydes. In such system, the rhodium catalyst generally is stabilized with a complex-forming agent, referred to in the art as a ligand, although use of a simple rhodium catalyst without such additional stabilizing agents also is known.

In one known arrangement, the rhodium complex catalyzed hydroformylation process is carried out in a non-aqueous hydroformylation reaction medium, the reaction-medium contains an organic solvent and both organic solvent-solubilized catalyst complex and solubilized free ligand, i.e., ligand not tied to bound to the rhodium catalyst complex. Organic solvents which do not interfere with the hydroformylation process are employed. Suitable organic solvents include those used in known Group VIII transition metal catalyzed processes such as alkanes, ethers, aldehydes ketones, esters, amides, aromatic hydrocarbons and mixtures of different organic solvents. Processes representative of such non-aqueous hydroformylation process are described in U.S. Pat. No. 3,527,809; U.S. Pat. Nos. 4,148,830 and 4,247,486; U.S. Pat. No. 4,260,828; U.S. Pat. No. 4,283,562; U.S. Pat. No. 4,306,087; U.S. Pat. No. 4,400,548; U.S. Pat. No. 4,429,161; U.S. Pat. No. 4,482,749; U.S. Pat. No. 4,491,675; U.S. Pat. No. 4,528,403; U.S. Pat. No. 4,593,011; U.S. Pat. No. 4,593,127; U.S. Pat. No. 4,599,206; U.S. Pat. No. 4,633,021; U.S. Pat. No. 4,668,651; U.S. Pat. No. 4,694,109; U.S. Pat. No. 4,716,250; U.S. Pat. No. 4,717,775; U.S. Pat. No. 4,731,486; U.S. Pat. No. 4,737,588; U.S. Pat. No. 4,748,261; European Patent Applications Publication Nos. 96,986; 96,987; and 96,988 (all published Dec. 28, 1983); PCT Applications Publication Nos. WO 80/01690 (published Aug. 21, 1980) and WO 87/07600 (published Dec. 17, 1987) to name a few. In these systems, product may be recovered by selective vaporization of the aldehyde under reduced pressure and at temperatures below about 150° C., preferably below about 130° C.

It also is known to use water or a similar polar solvent such as methanol as the catalytic reaction medium when hydroformylating olefins. One such process is described in U.S. Pat. No. 4,248,802, wherein water-soluble complexes of rhodium and certain salts of sulfonated triarylphosphines are used as the hydroformylation catalyst. Separation of aldehyde product from catalyst in this process is facilitated by the mutual immiscibility of product and catalyst solution. However, this approach typically requires more severe reaction conditions than the non-aqueous systems.

A new process also has been developed for recovering by a simple phase separation the aldehyde products which are produced when hydroformylating olefinic compounds in a non-aqueous reaction medium containing an ionic phosphorus ligand separate from the rhodium catalyst components. This process is described in copending application Ser. No. 218,911 entitled Process for Catalyst-Aldehyde Product Separation filed on Jul. 14, 1988 in the names of A. G. Abatjoglou, R. R. Peterson and D. R. Bryant.

In the case of both non-aqueous (non-polar) and aqueous (polar) hydroformylation processes, various rhodium-containing liquid streams may be generated that are not recirculated to the hydroformylation reactor. For example, in hydroformylation processes relying on phase separation to recover product aldehyde it is not uncommon for some of the rhodium to be removed with the aldehyde. The high cost and limited supply of rhodium make it imperative that rhodium loss via the aldehyde product be reduced to the lowest possible level. In fact, for economic operation, the rhodium concentration in the product aldehyde preferably should be reduced to less than about 50 parts per billion (ppb) and more preferably to less than about 20 ppb.

It is an object of the present invention, therefore, to provide a method for recovering Group VIII transition metals, such as rhodium from a liquid. It also is an object of the present invention to provide a method suitable for recovering Group VIII transition metals present at a very low concentration from a liquid. It is a particular object of the present invention to provide a method for recovering rhodium from a liquid, such as a hydroformylation aldehyde product.

BRIEF DESCRIPTION OF THE DRAWING

The sole FIGURE schematically illustrates a flow sheet of a transition metal, e.g. rhodium, recovery process according to the present invention.

DISCLOSURE OF THE INVENTION

The present invention is directed broadly to a method for recovering a Group VIII transition metal, such as rhodium, from a liquid containing a solution of the transition metal. The method comprises contacting such transition metal-containing liquid with an ion-exchange resin, said resin having bonded ionically thereto an organophosphorus ligand.

The present invention has broad applicability to the recovery of Group VIII transition metal from any polar or non-polar solution of the transition metal as may be derived from any transition metal process, such as for example, from processes for hydrogenating unsaturated compounds, such as copolymers of a conjugated diene and co-polymerizable monomers as described, for example, in U.S. Pat. Nos. 4,464,515 and 4,503,196, for carbonylating methanol to acetic acid, for oligomerizing olefins, for hydrocyanating butadiene to adiponitrile, for decarbonylating aldehydes for hydrosilylating olefins and other processes recognized by those skilled in the art. Thus, the present invention has broad applicability to the recovery of Group VIII transition metals, such as cobalt, nickel, rhodium, palladium, ruthenium, platinum and the like, from both polar and non-polar solutions containing such metals. For convenience in presentation, however, the invention will be described hereinafter with specific reference to the recovery of rhodium from liquid solutions derived from the hydroformylation of olefins and in particular from water-immiscible (non-polar) organic solutions derived therefrom. As noted above, the problem of rhodium loss, for example, via aldehyde product recovery, potentially confronts many of the hydroformylation processes known in the art. Those skilled in the art, however, will recognize the broad applicability of the present invention to the recovery of other transition metals and to other liquid streams generated by or derived from non-hydroformylation processes in view of the following description and specific examples.

The invention now will be described with reference to the sole figure. As shown, a polar or non-polar liquid stream 1 containing rhodium in solution is flowed through a column 10 containing an ion-exchange resin having bonded ionically thereto an organophosphorus ligand, referred to hereinafter simply as an "ionic ligand-functionalized resin". As the solution flows through the column 10 in contact with the ionic ligand-functionalized resin, rhodium is removed from the solution. Liquid having a reduced concentration of rhodium is recovered in line 2. Although not wishing to be bound to any particular explanation, it is believed that the rhodium forms a coordination complex with the ligand bonded ionically to the resin.

Any polar or non-polar, rhodium-containing liquid stream can be treated in accordance with the present invention and the invention is not limited to any particular liquid source. Both aqueous liquids, as well as other polar liquids such as methanol and polar and non-polar organic liquids such as aldehydes, alkanes, ethers, ketones, esters, amides and aromatics containing rhodium in solution can be treated for rhodium recovery in accordance with the present invention. Thus, for instance, the subject invention is useful for recovering rhodium present in the aldehyde product of any hydroformylation process or for that matter from any other liquid side stream containing rhodium that may be associated with or derived from a hydroformylation process. The invention is particularly useful for recovering rhodium from the aldehyde product of the hydroformylation process described in copending application Ser. No. 218,911 entitled Process for Catalyst Aldehyde Product Separation filed in the names of A. G. Abatjoglou, R. R. Peterson and D. R. Bryant on Jul. 14, 1988. As recognized by those skilled in the art, however, the treatment of certain rhodium-containing liquids may be better accomplished using certain resins due to resin composition-related physical constraints (e.g. solubility constraints, resin swelling constraints and the like).

Of course it is to be understood that the rhodium containing liquid starting material of this invention can also be a liquid residue derived from any other process designed to extract rhodium from a liquid. For example copending application Ser. No. 231,508 entitled Catalytic Metal Recovery From Non-Polar Organic Solutions filed in the names of D. J. Miller and D. R. Bryant on Aug. 12, 1988 now U.S. Pat. No. 4,935,550 is directed to recovering rhodium from a non-polar liquid, e.g. an aldehyde product, with an aqueous solution of an ionic phosphine ligand. The subject invention can be employed to recover trace amounts of rhodium left in the aldehyde starting material of such a process.

The rhodium concentration of the liquid to be treated in accordance with the present invention is not critical. Rhodium concentration does influence the rate of resin loading and other related parameters, however. While the invention may be used to remove rhodium from liquids having up to about 400 parts per million (ppm) rhodium, calculated as rhodium metal, or higher, it is especially useful for recovering lower amounts of rhodium e.g. less than about 20 ppm rhodium. More preferably, the rhodium-containing liquid treated in accordance with the present invention contains no more than about 2 ppm rhodium, most preferably below about 1 ppm rhodium, and may contain as little as 20 parts per billion (ppb) rhodium, i.e., simply a measurable amount of rhodium. Thus, if a liquid containing dissolved rhodium, such as an aldehyde product stream from a hydroformylation process, contains in excess of about 20 ppm rhodium, it may be more economical to extract the major portion of the rhodium from the liquid before contacting the liquid with the ionic ligand-functionalized ion-exchange resin in accordance with the present invention.

Ionic ligand-functionalized resins suitable for use in recovering rhodium from polar and non-polar liquid solution starting materials in accordance with the present invention can be prepared simply by contacting under ambient conditions an anion-exchange resin with an acidic or acidic salt derivative of an organophosphorus ligand or by contacting a cation-exchange resin with a basic or basic salt derivative of an organophosphous ligand. For convenience, such derivatives will be referred to herein simply as ionic organophosphorus ligands. For example, the ionic organophosphorus ligand generally can be dissolved in water or a polar solvent such as methanol and the solution subsequently contacted with the ion-exchange resin. Sufficient contacting is provided simply by mixing an aqueous slurry of the resin and a solution of the ligand, or by passing the ligand solution in contact with a bed of the resin. The contacting need only be sufficient for the ion-exchange resin to take up the ionic ligand from the solution, e.g. to exchange the original ionic moiety of the resin for the ionic ligand. Suitable conditions for carrying out this contacting can be identified using routine experimentation. Such contacting need only be sufficient to effect ion-exchange or reaction between the active sites of the resin and the ionic organophosphorous ligand. The resin then is separated from the aqueous solution and is appropriately washed and then dried as needed before use.

In the broad practice of the present invention, ionic organophosphorous ligands which can be used to prepare the ionic ligand-functionalized resin for use in the present invention can be any ionic organophosphine or ionic organophosphite which is capable of forming a coordination complex with rhodium in solution. Of course, the ionic moiety of the ligand cannot be positioned on the organophosphorus ligand in such a manner that the attachment of the ligand by ionic bonding to the resin interferes with the ability of the ligand to form a coordination complex with the transition metal, such as rhodium. The particular circumstances to be encountered in any intended application may influence which ionic organophosphorus ligand is most suitable. Ionic organophosphine ligands suitable for use in the present invention are well-known in the art, as are methods for their preparation and are further described in copending application Ser. No. 231,508 entitled Catalytic Metal Recovery From Non-Polar Organic Solutions filed in the name of D. J. Miller and D. R. Bryant on Aug. 12, 1988, the disclosure of which is incorporated herein by reference. Ionic organophosphite ligands suitable for use in the present invention are described in copending application Ser. No. 228,507 entitled Ionic Phosphites and Their Use in Homogeneous Transitions Metal Catalyzed Processes filed in the names of A. G. Abatjoglou and D. R. Bryant, on Aug. 5, 1988. The disclosure of which also is incorporated herein by reference.

Ionic organophosphine ligands as well as methods for their preparation, are well-known in the art and need not be described in great detail. Generally, the wide variety of ionic organophosphine ligands described in the prior art for use in the rhodium-catalyzed hydroformylation of olefins may be used. Certain suitable ionic organophosphines are those having the general formulae (1) and (2):

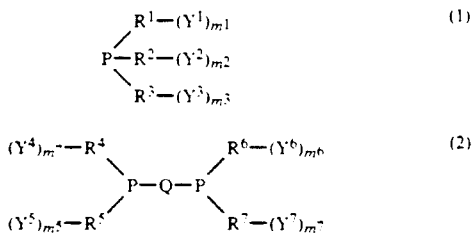

where $R^1$, $R^2$ and $R^3$ of formula (1) and $R^4$, $R^5$, $R^6$ and $R^7$ of formula (2) each individually represent a hydrocarbon radical containing from 1 to 30 carbon atoms selected from the group consisting of alkyl, aryl, alkaryl, aralkyl, and cycloalkyl radicals, where Q in formula (2) represents a divalent organic bridging group and where $Y^1$, $Y^2$ and $Y^3$ of formula (1) and, $Y^4$, $Y^5$, $Y^6$ and $Y^7$ of formula (2) are substituted on the hydrocarbon radical and each individually represents an ionic radical of overall neutral charge selected from the group consisting of:
- —$SO_3M$ wherein M represents inorganic or organic cationic atoms or radicals,
- —$PO_3M$ wherein M represents inorganic or organic cationic atoms or radicals,
- —$NR_3X'$ wherein each R represents a hydrocarbon radical containing from 1 to 30 carbon atoms selected from the class consisting of alkyl, aryl, alkaryl, aralkyl, and cycloalkyl radicals, and $X'$ represents inorganic or organic anionic atoms or radicals,
- —$CO_2M$ wherein M represents inorganic or organic cationic atoms or radicals, wherein $m^1$, $m^2$ and $m^3$ of formula (1) and $m^4$, $m^5$, $m^6$ and $m^7$ of formula (2) are integers which can be the same or different and which can range from 0 to 5. At least one of $m_1$, $m_2$ and $m_3$ and at least one of $m_4$, $m_5$, $m_6$ and $m_7$, cannot be zero (0), i.e. must be equal to or greater than 1. The integers $m_1$ through $m_7$ indicate the number of substituents on each hydrocarbon radical.

The hydrocarbon radicals, $R^1$, $R^2$ and $R^3$ of formula (1) and $R^4$, $R^5$, $R^6$ and $R^7$ of formula (2) preferably contain from 1 to 18 carbon atoms. Hydrocarbon radicals containing from 1 to 12 carbon atoms are more preferred. Such hydrocarbon radicals include those e.g. selected from the group consisting of alkyl, aryl, alkaryl, aralkyl and cycloalkyl. Illustrative hydrocarbon radicals are e.g. methyl, ethyl, propyl, butyl, hexyl, cyclohexyl, phenyl and the like. Most preferably, at least one of $R^1$, $R^2$ and $R^3$ in formula (1) and at least one of $R^4$, $R^5$, $R^6$ and $R^7$ in formula (2) is a phenyl radical. Such hydrocarbon radicals may contain one or more substituents provided that they do not unduly adversely affect the use of the ligand in this invention. Suitable substituents, in addition to the necessary ionic substituent, e.g., the sulfonate, carboxylate and the like, include straight and branched chain alkyl groups, preferably of 1 to 4 carbon atoms, alkoxy groups, halogen atoms, hydroxy, cyano, nitro and amino groups and the like. More preferably at least two, and most preferably three of $R^1$, $R^2$ and $R^3$ in formula (1) are phenyl groups and at least three and most preferably four of $R^4$, $R^5$, $R^6$ and $R^7$ in formula (2) are phenyl radicals.

The organic divalent bridging group represented by Q in the above formulas is a divalent radical containing from 1 to 30 carbon atoms selected from the group consisting of hydrocarbon radicals, oxygen containing hydrocarbon radicals (i.e. hydrocarbon radicals interrupted with an oxygen atom), sulfur containing hydrocarbon radicals (i.e. hydrocarbon radicals interrupted with a sulfur atom) and nitrogen containing hydrocarbon atoms (i.e. hydrocarbon radicals interrupted with a nitrogen atom). Preferably such radicals contain from 1 to 16 and more preferably from 1 to 12 carbon atoms. Illustrative divalent hydrocarbon radicals include alkylene radicals (e.g. methylene (—$CH_2$—), ethylene, propylene, isopropylene, butylene, 1,2-dimethylethylene, 1,1-dimethylethylene, neopentylene, 2-methylpropylene, hexylene, 2-ethylhexylene, dodecylene, eicosylene, and the like); arylene radicals (e.g. phenylene, substituted phenylene, diphenylene, substituted diphenylene, and the like); as well as alkylene containing arylene radicals (e.g. methylenephenylene (—$CH_2C_6H_4$—), ethylenephenylethylene (—$C_2H_4C_6H_4$—$C_2H_4$—), phenylenepropylphenylene (—$C_6H_4C(CH_3)_2C_6H_4$—), methylenediphenylmethylene (—$CH_2C_6H_4C_6H_4CH_2$—), and the like); alkylidene radicals (e.g. ethylidene (—$CH=CH$—), and the like); and the like. Illustrative oxygen containing hydrocarbon radicals include alkyleneoxyalkylene radicals (e.g. ethyleneoxymethylene (—$C_2H_4OCH_2$—), propyleneoxymethylene (—$C_3H_6OCH_2$—), ethyleneoxyethylene (—$C_2H_4OC_2H_4$—), 1,2-bis(ethyleneoxy)ethane (—$C_2H_4OC_2H_4OC_2H_4$—), propyleneoxypropylene (—$C_3H_6OC_3H_6$—) and the like); aryleneoxyalkylene radicals (e.g. phenyleneoxymethylene (—$C_6H_4OCH_2$—), and the like); and the like. Illustrative sulfur or thio containing hydrocarbon radicals include alkylenethioalkylene radicals (e.g. ethylenethioethylene (—$C_2H_4SC_2H_4$—), 1,2-bis(ethylenethio)ethane (—$C_2H_4SC_2H_4SC_2H_4$—), propylenethiomethylene (—$C_3H_6SCH_2$—), propylenethiopropylene (—$C_3H_6SC_3H_6$—), and the like); arylenethioalkylene radicals (e.g. phenylenethiomethylene (—$C_3H_6S$—$CH_2$—), and the like); and the like. Illustrative amino containing hydrocarbon radicals include alkyleneaminoalkylene radicals (e.g. methyleneaminomethylethylene (—$CH_2N(CH_3)C_2H_4$—), ethyleneaminomethylethylene (—$C_2H_4N(CH_3)C_2H_4$), bis(ethyleneaminomethyl)ethane (—$C_2H_4N(CH_3)C_2H_4N(CH_3)C_2H_4$—), propyleneamino methylpropylene (—$C_3H_6N(CH_3)C_3H_6$—) and the like; and the like. Most preferably Q is a divalent hydrocarbon radical, especially a divalent alkylene radical containing from 2 to 8 carbon atoms.

Particularly, suitable ionic organophosphine ligands are the ionic triarylphosphines and, in particular, sulfonated and carboxylated triarylphosphines, as, for example, are described in U.S. Pat. Nos. 4,248,802; 4,399,312; 4,668,824; 4,716,250 and 4,731,486 and European Patent Application Pub. No. 216,315 (published April 1987). Preferred among this group are the monosulfonated and trisulfonated triphenylphosphines and their salts, and the monocarboxylated and tricarboxylated triphenylphosphines and their salts. Another suitable class of ionic organophosphines are ionic bisdiarylphosphines such as bisdiphenylphosphinoethane monosulfonates. Mixtures of suitable ionic phosphine ligands also can be employed.

Such ionic organophosphine ligands capable of forming a coordination complex with rhodium embraced by the above formulae, as well as methods for their preparation, are well-known in the art and need not be described in detail. See for example J. Chem. Soc. (1958), pp. 276-288 and U.S. Pat. Nos. 4,248,802; 4,399,312; 4,483,802; 4,633,021; 4,668,824; 4,716,250 and 4,731,486, and European Patent Application, Pub. No. 216,315 (published April 1987) all incorporated herein by reference. For example sulfonated ligands may be prepared by sulfonating the corresponding phosphine, e.g. triphenylphosphine, with fuming sulfuric acid (oleum) under controlled temperature conditions.

As suitable counter-ions, M, for the anionic moieties of the ionic phosphines there can be mentioned hydrogen (i.e. a proton), the cations of the alkali and alkaline earth metals, e.g., lithium, sodium, potassium, cesium, rubidium, calcium, barium, magnesium and strontium, the ammonium cation and quaternary ammonium cations. Suitable anionic atoms or radicals include, for example, sulfate, carbonate, phosphate, chloride, acetate, oxalate and the like. Of course it is understood that the number of anionic and cationic moieties in a ligand molecule also depends on the valences of the ions (ionic radical) and counter-ions (M and X') of any particular ligand.

Ionic organophosphite ligands suitable for use in the present invention are selected from the group consisting of (i) poly-phosphites having the formula

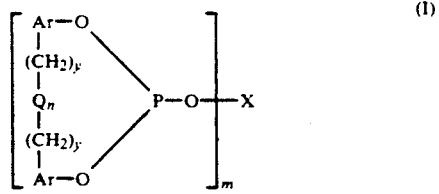

wherein each Ar group represents an identical or different aryl radical; wherein X represents an m-valent hydrocarbon radical selected from the group consisting of alkylene, alkylene-oxy-alkylene, aryl, and aryl-$(CH_2)_y$—$(Q)_n$—$(CH_2)_y$-aryl; wherein each y individually has a value of 0 or 1; wherein each Q individually represents a divalent bridging group selected from the class consisting of —$CR^1R^2$—, —O—, —S—, —$NR^3$—, —$SiR^4R^5$—, and —CO—, wherein $R^1$ and $R^2$ each individually represents a radical selected from the group consisting of hydrogen, alkyl of 1 to 12 carbon atoms, phenyl, tolyl and anisyl, wherein $R^3$, $R^4$, and $R^5$ each individually represents —H or —$CH_3$; wherein each n individually has a value of 0 to 1; wherein m has a value of 2 to 6; and wherein the poly-phosphites of formula (I) contain at least one ionic moiety selected from the same group of ionic radicals of overall neutral charge identified above in connection with the ionic organophophines substituted on an aryl moiety of Ar or X;

(ii) diorganophosphites having the formula

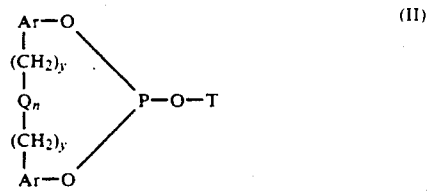

wherein T represents a monovalent hydrocarbon radical; wherein Ar, Q, n, and y are as defined above; and wherein the diorganophosphites of formula (II) contain at least one moiety selected from the same group of ionic radicals of overall neutral charge identified above in connection with the ionic organophosphines substituted on an aryl moiety of Ar or T; and (iii) open-ended bis-phosphites having the formula

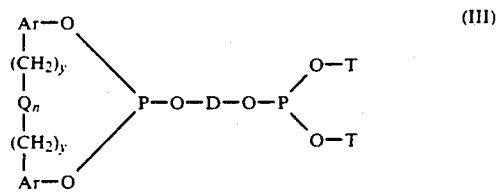

wherein D represents a divalent bridging group selected from the group consisting of alkylene, alkylene-oxy-alkylene, aryl, and aryl-$(CH_2)_y$—$Q_n$—$(CH_2)_y$-aryl; wherein Ar, Q, n, y, and T are as defined above and each T may be identical or different; and wherein the bisphosphites of formula (III) contain at least one ionic moiety selected from the same group of ionic radicals of overall neutral charge identified above in connection with the ionic organophosphines substituted on an aryl moiety of Ar, D or T.

Illustrative aryl radicals of the above-defined Ar, X, D and T groups of the above formulae include aryl moieties which may contain from 6 to 18 carbon atoms such as phenylene, naphthylene, anthracylene, and the like.

Moreover, as noted above, while any given ionic phosphite in the above formulae must contain at least one ionic moiety selected from the same group of ionic radicals of overall neutral charge identified above in connection with the ionic organophosphines substituted on an aryl moiety of the above defined Ar, X, D and T groups, it is to be understood that any given phosphite may contain more than one such ionic moiety and such may also be the case with regard to any given aryl moiety in each ionic phosphite, provided that the total number of such ionic moieties in the given phosphite is not so high as to unduly adversely affect utility of the ionic phosphite ligand for bonding to the resin and for coordinating rhodium. Thus, each ionic phosphite ligand generally contains from 1 to 3 such ionic moieties. It is preferred that only one such ionic moiety be substituted on any given aryl moiety in the ionic phosphite ligand when the ligand contains more than one such ionic moiety.

In the above organophosphite formulae, preferably, m is from 2 to 4, and each y and each n has a value of 0. However, when n is 1, Q preferably is a —CR$^1$R$^2$— bridging group as defined above and more preferably methylene (—CH$_2$—) or alkylidene (—CHR$^2$—), wherein R$^2$ is an alkyl radical of 1 to 12 carbon atoms (e.g. methyl, ethyl, propyl, isopropyl, butyl, dodecyl, etc.), especially methyl.

The m-valent hydrocarbon radicals represented by X in the ionic poly-phosphite ligands of formula I above are hydrocarbons containing from 2 to 30 carbon atoms selected from the group consisting of alkylene, alkylene-oxy-alkylene, aryl, and aryl-(CH$_2$)$_y$—(Q)$_n$—(CH$_2$)$_y$-aryl radicals, wherein Q, n and y are the same as defined above. Preferably the alkylene moieties of said radicals contain from 2 to 18 carbon atoms and more preferably from 2 to 12 carbon atoms, while the aryl moieties of said radicals preferably contain from 6 to 18 carbon atoms.

The divalent bridging group represented by D in the open-ended bis-phosphite ligands of formula III above are divalent hydrocarbons containing from 2 to 30 carbon atoms selected from the group consisting of alkylene, alkylene-oxy-alkylene, aryl and aryl-(CH$_2$)$_y$—(Q)$_n$—(CH$_2$)$_y$-aryl radicals, wherein Q, n and y are the same as defined above. Preferably the alkylene moieties of said radicals contain from 2 to 18 carbon atoms and more preferably from 2 to 12 carbon atoms, while the aryl moieties of said radicals preferably contain from 6 to 18 carbon atoms.

Hydrocarbon radicals represented by T in the above ionic phosphite ligand formulae include monovalent hydrocarbon radicals containing from 1 to 30 carbon atoms selected from the group consisting of alkyl radicals including linear or branched primary, secondary, or tertiary alkyl radicals, such as methyl, ethyl, n-propyl, isopropyl, amyl, sec-amyl, t-amyl, 2-ethylhexyl, and the like; aryl radicals such as phenyl, naphthyl, and the like; aralkyl radicals such as benzyl, phenylethyl, tri-phenylmethylethane, and the like; alkaryl radicals such as tolyl, xylyl, and the like; and cycloalkyl radicals such as cyclopentyl, cyclohexyl, cyclohexylethyl, and the like.

Preferably, T is selected from the group consisting of alkyl and aryl radicals which contain from about 1 and 30 carbon atoms. Preferably, the alkyl radicals contain from 1 to 18 carbon atoms, most preferably from 1 to 10 carbon atoms, while the aryl, aralkyl, alkaryl, and cycloalkyl radicals preferably contain from 6 to 18 carbon atoms. Further, although each T group in an ionic phosphite molecule of formula (III) may differ from the other, preferably they are identical.

Of course it is to be further understood that in addition to being substituted with an ionic moiety as described above, the aryl moieties of the defined Ar, X, D and T groups in the above formulae may also be substituted with any other substituent radical that does not unduly adversely affect the process of this invention. Illustrative substituents include radicals containing from 1 to 18 carbon atoms such as alkyl, aryl, aralkyl, alkaryl and cycloalkyl radicals; alkoxy radicals; silyl radicals such as —Si(R$^9$)$_3$ and —Si(OR$^9$)$_3$; amino radicals such as —N(R$^9$)$_2$; acyl radicals such as —C(O)R$^9$; acyloxy radicals such as —OC(O)R$^9$; carbonyloxy radicals such as —COOR$^9$; amido radicals such as —C(O)N(R$^9$)$_2$ and —N(R$^9$)COR$^9$; sulfonyl radicals such as —SO$_2$R$^9$; sulfinyl radicals such as —SO(R$^9$)$_2$; thionyl radicals such as —SR$^9$; phosphonyl radicals such as —P(O)(R$^9$)$_2$; as well as halogen, nitro, cyano, trifluoromethyl, and hydroxy radicals, and the like, wherein each R$^9$ can be a monovalent hydrocarbon radical such as alkyl, aryl, alkaryl, aralkyl, and cycloalkyl radicals, with the provisos that in amino substituents such as —N(R$^9$)$_2$, each R$^9$ taken together can also comprise a divalent bridging group that forms a heterocyclic radical with the nitrogen atom, in amido substituents such as —C(O)N(R$^9$)$_2$ and —N(R$^9$)COR$^9$, each R$^9$ bonded to N can also be hydrogen, and in phosphonyl substituents such as —P(O)(R$^9$)$_2$, one R$^9$ can be hydrogen. Of course, it is to be understood that each R$^9$ group in a particular substituent may be the same or different. Of course, such hydrocarbon substituent radicals could possibly in turn be substituted with a substituent such as already herein outlined above provided that any such occurrence would not unduly adversely effect the present invention.

Among the more preferred ionic phosphite ligands are those wherein the two Ar groups linked by the bridging group represented by —(CH$_2$)$_y$—(Q)$_n$—(CH$_2$)$_y$— in the above formulae are bonded through their ortho positions in relation to the oxygen atoms that connect the Ar groups to the phosphorus atom. It is also preferred that any substituent radial, when present on such Ar groups, be bonded in the para and/or ortho position on the aryl in relation to the oxygen atom that bonds the substituted Ar group to its phosphorus atom.

Accordingly, a preferred class of ionic phosphite ligands employable in this invention are those of the formulae:

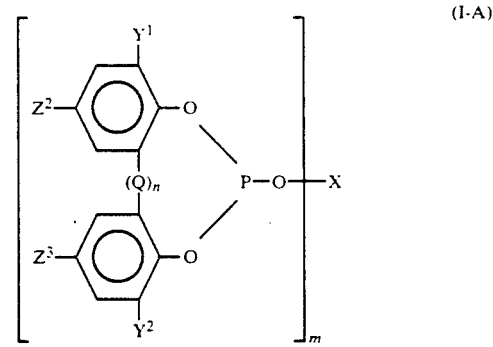

(I-A)

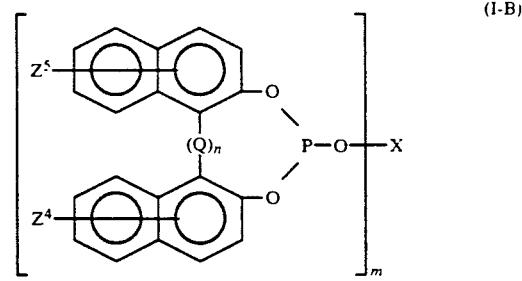

(I-B)

wherein each Y$^1$, Y$^2$, Z$^2$, Z$^3$, Z$^4$ and Z$^5$ group individually represents a radical selected from the group consisting of hydrogen, monovalent hydrocarbon radicals containing from 1 to 18 carbon atoms (e.g. alkyl, aryl, alkaryl, aralkyl, and cycloalkyl radicals), hydroxy, alkoxy radicals containing from 1 to 10 carbon atoms, and sulfonic acid and carboxylic acid moieties and their salts; wherein X represents an m-valent bridging group containing from 6 to 30 carbon atoms selected from the group consisting of aryl and aryl-$Q_n$-aryl radicals; wherein m has a value of 2 to 4; wherein each Q radical individually represents —$CR^1R^2$— wherein $R^1$ and $R^2$ each individually represent a radical selected from the group consisting of hydrogen and alkyl of 1 to 12 carbon atoms; and wherein n has a value of 0 or 1; with the proviso that in each phosphite ligand of formulae I-A and I-B above, either at least one $Y^1$, $Y^2$, $Z^2$, $Z^3$, $Z^4$ and $Z^5$ group is an ionic moiety selected from the group consisting of sulfonic acid and carboxylic acid moieties and their salts, or each said ligand contains at least one such ionic moiety substituted on an aryl moiety of X.

Another preferred class of ionic phosphite ligands employable in this invention are those of the formulae

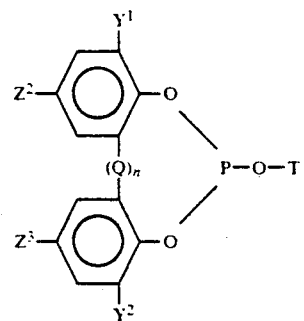

(II-A)

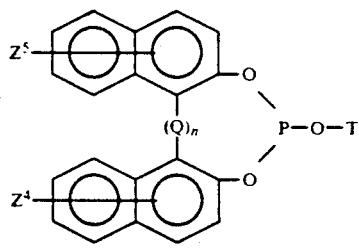

(II-B)

wherein $Y^1$, $Y^2$, $Z^2$, $Z^3$, $Z^4$, $Z^5$, Q and n are the same as defined above in formulae I-A and I-B; wherein T represents a monovalent hydrocarbon radical containing from 1 to 30 carbon atoms selected from the group consisting of alkyl, aryl, aralkyl, alkaryl or cycloalkyl radicals; with the proviso that in each phosphite ligand of formulae II-A and II-B above, either at least one $Y^1$, $Y^2$, $Z^2$, $Z^3$, $Z^4$ and $Z^5$ group is an ionic moiety selected from the group consisting of sulfonic acid and carboxylic acid moieties and their salts, or each said ligand contains at least one such ionic moiety substituted on an aryl moiety of T.

Yet another preferred class of ionic phosphite ligands employable in this invention are those of the formulae

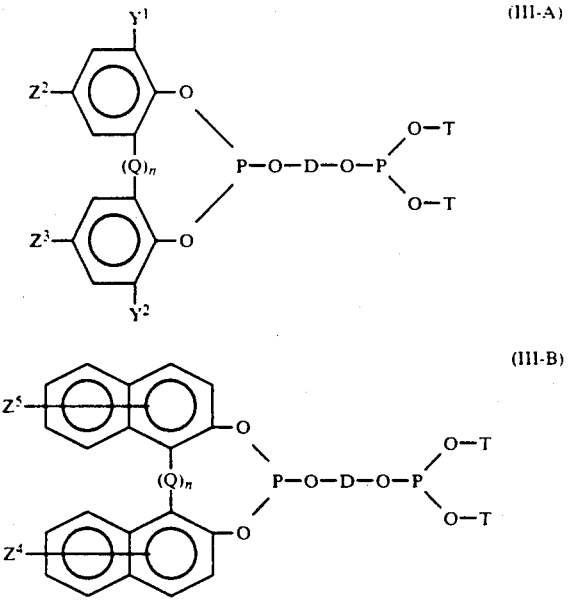

wherein D represents a divalent bridging group containing from 6 to 30 carbon atoms selected from the group consisting of aryl and aryl-$Q_n$-aryl radicals; and wherein $Y^1$, $Y^2$, $Z^2$, $Z^3$, $Z^4$, $Z^5$, Q, n and each T are the same as defined above in formulas I-A, I-B, II-A and II-B; and wherein each T can be the same or different; with the proviso that in each phosphite ligand of formulas III-A and III-B above, either at least one $Y^1$, $Y^2$, $Z^2$, $Z^3$, $Z^4$, and $Z^5$ group is an ionic moiety selected from the group consisting of sulfonic acid and carboxylic acid moieties and their salts, or each said ligand contains at least one such ionic moiety substituted on an aryl moiety of D or T.

A number of preferred embodiments of the above ionic phosphite ligand formulae may be found already herein discussed above, e.g. most preferably m has value of 2 and each y and n has a value of 0, while Q is preferably —$CH_2$— or —$CHCH_3$—. Further each ionic phosphite generally contains from 1 to 3 such ionic moieties as defined herein.

The ionic moieties of the preferred ionic phosphite ligand formulae above are sulfonic acid and carboxylic acid moieties and their salts. Such salts contain that number of organic or inorganic cations needed to balance the charge of the acid anions substituted onto the phosphite ligand. The same counter-ions disclosed in connection with the ionic phosphines are suitable. Thus, suitable inorganic cations may be selected from the group consisting of alkali metals, alkaline earth metals and the ammonium cation. Illustrative alkali metal cations include lithium (Li+), sodium (Na+), potassium (K+), cesium (Cs+), and rubidium (Rb+), while illustrative alkaline earth metal cations include calcium (Ca++), barium (Ba++), magnesium (Mg++), and strontium (Sr++). Suitable organic cations may be selected from the group consisting of quaternary ammonium cations such as those having the formula [N($R^{21}$)($R^{22}$)($R^{23}$)($R^{24}$)]+, wherein $R^{21}$, $R^{22}$, $R^{23}$, and $R^{24}$ each represents hydrogen or a radical containing from 1 to 30 carbon atoms selected from the group consisting of alkyl, aryl, alkaryl, aralkyl, and cycloalkyl radicals, and wherein any two or three of said $R^{21}$, $R^{22}$, $R^{23}$, and $R^{24}$ groups can be bonded together to form a mono-, bi-, or poly-cyclic ring along with the nitrogen atom of said cation.

Illustrative m-valent hydrocarbon radicals represented by X in the above formulae include substituted and unsubstituted hydrocarbon radicals containing from 2 to about 30 carbon atoms selected from the group consisting of alkylene, alkylene-oxy-alkylene, phenylene, naphthylene, phenylene-$(CH_2)_y$—$(Q)_n$—$(CH_2)_y$-phenylene and naphthylene-$(CH_2)_y$—$(Q)_n$—$(CH_2)_y$-naphthylene radicals, and where Q, n, and y are the same as defined above. More specific illustrative m-valent hydrocarbon radicals represented by X include e.g. straight or branched chain alkylene radicals such as —$(CH_2)_x$ wherein x has a value of 2 to 18 (preferably 2 to 12), pentaerythritol, which yields an m-valent hydrocarbon radical of formula $C(CH_2OH)_{4-m}(CH_2)m$, 1,2,6-hexylene, and the like; —$CH_2CH_2OCH_2CH_2$—; 1,4-phenylene, 2,3-phenylene, 1,3,5,-phenylene, 1,3-phenylene, 1,4-naphthylene, 1,5-naphthylene, 1,8-naphthylene, 2,3-naphthylene, 1,1'-biphenyl-2,2'-diyl, 2,2'-biphenyl-1,1'-diyl, 1,1'-biphenyl-4,4'-diyl, 1,1'-binaphthyl-2,2'-diyl, 2,2-binaphthtyl-1,1'-diyl, phenylene-$CH_2$-phenylene, phenylene-S-phenylene, $CH_2$-phenylene-$CH_2$, phenylene-$CH(CH_3)$-phenylene radicals and the like.

Preferred ionic poly-phosphite ligands of formula (I) include close-ended bis-phosphites wherein X in the above ionic phosphite formulae is a divalent radical selected from the group consisting of phenylene, naphthylene, naphthylene-$(Q)_n$-naphthylene, and phenylene-$(Q)_n$-phenylene radicals, wherein Q and n are the same as both generically and preferably defined above. Of course the aryl moieties of such X radicals can contain substituent radicals such as disclosed and discussed herein.

Divalent radical D in ionic phosphite formula (III) above can be the same as any m-valent radical, as described for X herein, wherein $m=2$. Further preferred open-ended bis-phosphite ligands include those wherein D is a divalent radical selected from the group consisting of phenylene, naphthylene, naphthylene-$(Q)_n$-naphthylene, and phenylene-$(Q)_n$-phenylene radicals wherein Q and n are the same as both generically and preferably defined above. Of course the aryl moieties of such D radicals can contain substituent radicals such as disclosed and discussed herein.

Among the more preferred bis-phosphite ligands of formula (I) and open-ended bis-phosphite ligands of formula (III) are those wherein the naphthylene radical represented by X or D is selected from the group consisting of 1,2-naphthylene, 2,3-naphthylene, and especially 1,8-naphthylene, and those wherein the two phenylene radicals or two naphthylene radicals of X or D linked by the bridging group represented by —$(Q)_n$— are bonded through their ortho positions in relation to the oxygen atoms that connect the two phenylene or two naphthylene radicals to their phosphorus atom. It is also preferred than any substituent radical when present on such phenylene or naphthylene radicals be bonded in the para and/or ortho position of the phenylene or naphthylene radical in relation to the oxygen atom that bonds the given substituted phenylene or naphthylene radical to its phosphorus atom.

Hydrocarbon radicals represented by T in the above ionic phosphite ligand formulae include monovalent hydrocarbon radicals containing from 1 to 30 carbon atoms selected from the group consisting of alkyl radicals including linear or branched primary, secondary, or tertiary alkyl radicals, such as methyl, ethyl, n-propyl, isopropyl, amyl, sec-amyl, t-amyl, 2-ethylhexyl, 1-decyl, and the like; aryl radicals such as phenyl, naphthyl, and the like; aralkyl radicals such as benzyl, phenylethyl, tri-phenylmethylethane, and the like; alkaryl radicals such as tolyl, xylyl, and the like; and alicyclic radicals such as cyclopentyl, cyclohexylethyl, and the like.

Preferably, T is selected from the group consisting of alkyl and aryl radicals which contain between about 1 to 30 carbon atoms. Preferably, the alkyl radicals contain from 1 to 18 carbon atoms, most preferably from 1 to 10 carbon atoms, while the aryl, aralkyl, alkaryl, and alicyclic radicals preferably contain from 6 to 18 carbon atoms. Further, although each T group in an ionic phosphite molecule of formula (III) may differ from the other, preferably they are identical.

Further preferred aryl radicals represented by T include those having the formula

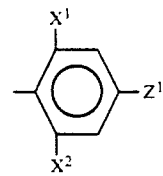

wherein $X^1$, $X^2$, and $Z^1$ each individually represents a radical as defined for $Y^1$, $Y^2$, $Z^2$ and $Z^3$ hereinbefore. More preferably $X^1$ and $X^2$ are the same or different and represent hydrogen or a radical having a steric hindrance of isopropyl or greater and $Z^1$ represents an ionic moiety as defined herein.

Moreover, as noted, the above-described radicals represented by Ar, X, D and T of the above formulae, may be further substituted with any substituent that does not unduly adversely effect the desired results of this invention. Illustrative substituents are, for example, monovalent hydrocarbon radicals having between one and about 18 carbon atoms, such as alkyl, aryl, alkaryl, aralkyl, cycloalkyl and other radials, as defined above. In addition various nonhydrocarbon substituents that may be present include e.g. halogen, preferably chlorine or fluorine, —$NO_2$, —CN, —$CF_3$, —OH, —$Si(CH_3)_3$, —$Si(OCH_3)_3$, —$Si(C_3H_7)_3$, —$C(O)CH_3$, —$C(O)C_2H_5$, —$OC(O)C_6H_5$, —$C(O)OCH_3$, —$N(CH_3)_2$, —$NH_2$, —$NHCH_3$, —$NH(C_2H_5)$, —$CONH_2$, —$CON(CH_3)_2$, —$S(O)_2C_2H_5$, —$OCH_3$, —$OC_2H_5$, —$OC_6H_5$, —$C(O)C_6H_5$, —$O(t—C_4H_9)$, —$SC_2H_5$, —$OCH_2CH_2OCH_3$, —$(OCH_2CH_2)_2OCH_3$, —$(OCH_2CH_2)_3OCH_3$, —$SCH_3$, —$S(O)CH_3$, —$SC_6H_5$, —$P(O)(C_6H_5)_2$, —$P(O)(CH_3)_2$—$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, —$NHC(O)CH_3$, and the like. Moreover, each Ar, X, D and T group may contain one or more such substituent groups which may also be the same or different in any given ligand molecule. Preferred substituent radicals include alkyl and alkoxy radicals containing from 1 to 18 carbon atoms and more preferably from 1 to 10 carbon atoms, especially t-butyl and methoxy.

Substitution (excluding the bridging group —$(CH_2)_y$—$(Q)_n$—$(CH_2)_y$— when present) at the ortho positions of the aryl groups of the Ar, X, D and T groups of the above formulae relative to the oxygen atom that bonds each aryl group to a phosphorus atom of the ionic phosphite ligand, may influence the stability of the ligand due to steric hindrance around the phosphorus atom of the ionic phosphite ligand caused by substitution in such ortho positions. For example, too much steric hindrance may affect the ability of the ionic phosphite ligand to bond to the Group VIII transition metal (e.g. rhodium), while not enough steric hindrance may cause the ionic phosphite to bond too strongly. Steric hindrance may also effect the bonding of the ligand to the ion-exchange resin.

One class of preferred ligands of the above formulae are those designated as I-A, II-A and III-A above, wherein both $Y^1$ and $Y^2$ are radicals having a steric hindrance of at least isopropyl or greater such as branched chain alkyl radicals having three to five carbon atoms, especially t-butyl, while more preferably $Z^2$ and $Z^3$ are both alkoxy radicals, especially methoxy.

The ionic phosphite ligands employable in this invention can be readily prepared via a series of conventional phosphorus halide-alcohol condensation reactions. Such types of condensation reactions and the manner in which they may be conducted are known in the art as seen for example by U.S. Pat. Nos. 4,599,206 and 4,717,775 directed to nonionic type diorganophosphite ligands of Formula (II) above; U.S. Pat. No. 4,748,261 directed to nonionic type open-ended, bis-phosphite ligands of Formula (III) above; and U.S. Pat. No. 4,668,651 directed to nonionic type poly-phosphite ligands of Formula (I) above. For instance, the method for preparing ionic diorganophosphite ligands of Formula (II) above can comprise reacting a corresponding organic diol (dihydroxy) compound with phosphorus trichloride to form an organic phosphorochloridite intermediate which in turn is reacted with a corresponding organic mono-ol (monohydroxy) compound to produce the desired ionic diorganophosphite ligand. Optionally such ligands can be prepared in reverse order, for instance, from a corresponding organic phosphorochloridite and a corresponding diol compound. Likewise ionic open-ended bis-phosphite ligands of Formula (III) above can be prepared by (a) reacting a corresponding organic dihydroxy compound with phosphorus trichloride to form a corresponding organic phosphorochloridite intermediate, (b) reacting said intermediate with an organic diol (corresponding to D in Formula (III) above) to form a corresponding hydroxy substituted diorganophosphite intermediate, (c) reacting said hydroxy substituted diorganophosphite intermediate with phosphorus trichloride to form the corresponding organic phosphorodichloridite intermediate and (d) reacting said dichloridite with two moles of a corresponding organic mono-ol compound (or one mole each of two different mono-ols) to arrive at the corresponding desired ionic, open-ended bis-phosphite ligand. Such condensation reactions may also be carried out in a single-pot synthesis, if desired. Further ionic poly-phosphite ligands of Formula (I) above can be prepared by the same type of phosphorus halide-alcohol condensation reactions as noted above for preparing the ionic ligands of Formula (III) above, for instance, employing, e.g. a diol in step (b) above corresponding to X in Formula (I) and reacting the dichloridite intermediate of step (d) above with a corresponding diol instead of two moles of a mono-ol, to produce the desired ionic poly-phosphite ligand. Alternatively such ionic poly-phosphites could be prepared by a single-pot synthesis, e.g. by reacting the corresponding organic phosphorochloridite intermediate of step (a) above or a mixture of different corresponding chloridite intermediates with a polyol corresponding to X, the mole amount of chloridite employed being equal to the number of hydroxy groups on the polyol employed. For example two mole equivalents of the same phosphorochloridite intermediate of step (a) above (or one mole each of two different such intermediates) could be reacted with one mole equivalent of a diol corresponding to X to form a close-ended bis-phosphite type ligand.

Moreover, since the ionic phosphite ligands as defined in this invention must contain at least one ionic moiety, selected from the same group of ionic radicals of overall neutral charge identified above in connection with the ionic organophosphines, substituted on an aryl radical, it is preferred that at least one of the organic reactants or intermediates of the halide-alcohol condensation reactions employable in preparing such ionic ligands contain at least one such ionic moiety substituted on an aryl moiety, though it may be possible to provide such ionic moieties after the production of a nonionic phosphite ligand by conventional procedures, e.g. known sulfonation techniques, carboxylation techniques and the like. Salts of sulfonated acids, carboxylated acids and the like of simple hydroxy compounds, such as phenolic and naphtholic mono-ols and diols, and/or methods for their preparation are known.

Moreover, while such phosphorus halide-alcohol condensation reactions may be carried out in the presence of a solvent e.g. toluene and a HCl acceptor e.g. an amine, it is a preferred to employ double salts of ionic mono-ol reactants and triple salts of ionic diol reactants in the presence of a dipolar aprotic solvent such as N-methyl pyrolidone (NMP), dimethyl sulfoxide (DMSO), dimethyl formamide (DMF), sulfolane, and the like, when such ionic type reactants are condensed with a desired phosphorus-halide containing moiety e.g. $PCl_3$, phosphorochloridite or phosphorodichloridite compound in order to avoid the need for any HCl acceptor. Such double or triple salts and/or methods for their preparation are well known.

For example, one starting material could be the double salt of phenol p-sulfonic acid or the double salt of hydroxy p-benzoic acid, e.g. depending upon whether the sulfonate or carboxylate form of the ionic phosphite is desired. Other suitable starting materials will be obvious to those skilled in the art and these materials may be substituted or unsubstituted at other sites on the benzene ring. The double salt (e.g. phenolate sulfonate or phenolate carboxylate) can be prepared by addition of suitable basic material, such as sodium hydroxide or potassium hydroxide, to the corresponding starting mono-ol material. Formation of the double salt conveniently can be carried out in a solution of starting material and base in aprotic solvent and water. The water may be provided by an aqueous solution of the base.

The water then is removed from the solution of the double salt e.g. by azeotropic distillation with toluene. For example, a sufficient quantity of toluene is thoroughly mixed with the solution containing the double salt, to form a toluene/water azeotrope having boiling point of about 85° C. at atmospheric pressure. The azeotropic composition contains about 80% toluene and 20% water. The aprotic solvent and the double salt have a low volatility at these conditions, and so are easily separated from the toluene/water azeotrope.

Because the double salt is essentially insoluble in aprotic solvent, a suspension of double salt in aprotic solvent forms as the azeotropic composition is removed. This suspension then is reacted with a desired phosphorhalide intermediate. i.e., with an organic phosphorochloridite or phosphorodichloridite. The anion of the hydroxy group of the double salt selectively reacts with the phosphorous moiety of the phosphorohalide intermediate to yield the desired ionic phosphite which is readily soluble in the aprotic solvent. By-product cation/halide salt is not soluble in the aprotic solvent, and can be removed by filtration or any soluble solid/liquid separation technique known in the art, e.g., centrifugation.

The ionic phosphite composition can be easily separated from the aprotic solvent, e.g. by removing the aprotic solvent from the mixture under vacuum distillation conditions. The thus recovered ionic phosphite material can be further purified by recrystallization in ways known to those skilled in the art and the purified ionic phosphite material utilized in this invention. Other ionic phosphites employable in this invention can be readily prepared by those skilled in the art employing similar techniques.

The ionic phosphine and ionic phosphite ligands employable in this invention preferably are used in their free-acid form. i.e. where M is a cationic hydrogen atom (proton). The salts of the ionic organophosphines and ionic organophosphites can be converted to the free-acid form of the ligand using known procedures. For example, the use of ion-exchange is illustrated in the subsequent examples.

Anion-exchange and cation-exchange resins suitable for preparing the ionic ligand-functionalized resin employable in the present invention include the wide variety of insoluble organic polymers obtained by addition-polymerization or poly-condensation of suitable monomers and heretofore used for preparing ion exchange resins. These organic polymers then are modified subsequently, using techniques well-known to those skilled in the art to provide the desired ion-exchange capability. Insolubilization of suitable polymers typically is achieved by chemical crosslinking, by radiation or by thermosetting. Examples of suitable polymers for the ion-exchange resin are polystyrene, polyethylene, polyvinyl chloride, polyvinyl acetate, polyethylene imine and other polyalkylene imines, polyvinyl pyridine, polyacrylonitrile, polyacrylates, Saran®, Teflon® and the like. Suitable crosslinking agents for ensuring insolubility, particularly for polyolefins, are divinylbenzene, butadiene, diallyl maleate, diallyl phthalate, glycol dimethacrylate, and other di- or triolefins.

Condensation polymers suitable for preparing the ion exchange resin include phenol-formaldehyde resins, urea-formaldehyde resins, alkyd resins (reaction products of polyhydric alcohols and polybasic acids), polyesters, such as Dacron® and polyamides. Also suitable are polyamines, polyethers such as polyphenyl oxide, polystyrene oxide or polypropylene oxide, polysulfides such as polyphenyl sulfide, and polysulfones such as polyphenyl sulfone. Mixtures of copolymers also are suitable. Celluloses also are included although they are not normally considered resins. These resins are modified using techniques known to those skilled in the ion-exchange art, to provide the resin with its ion-exchange capacity.

A particularly useful resin is a commercially available copolymer of styrene and divinylbenzene. Such resins are characterized by having long chains of polystyrene locked together by means of divinylbenzene crosslinks into a three-dimensional, insoluble polymeric phase. However, as previously indicated, in the broad practice of the present invention the particular resin used is not critical.

Anion-exchange and cation-exchange resins are available in both the gellular and macrorecticular form. While both gellular and macroreticular forms of the resin can be used in the present invention, it is preferred to use macroreticular resins. Generally, macroreticular resins have a substantially uniform macropore structure with average pore diameters above about 50 $\mu$m. Gellular resins generally should be used only if the liquid containing the metal to be removed in carrying out the present invention will cause the gellular resin to swell, which increases the available surface area of the resin, as recognized by those skilled in the ion-exchange resin art.

Anion-exchange resins are characterized as either strong base or weak base anion-exchange resins depending on the active ion-exchange sites of the resin. Both strong base and weak base anion-exchange resins can be used to prepare the ionic ligand-functionalized resin used in connection with the present invention.

Strong base anion-exchange resins consist of polymers having mobile monovalent anions, such as hydroxide (OH$^-$) and the like associated for example with covalently bonded quaternary ammonium, phosphonium or arsonium functional groups or tertiary sulfonium functional groups. These functional groups are known as active sites and are distributed over the surface of the resin particle. Strong base anion-exchange resins have the capacity to undergo ion exchange independent of the pH of the medium by virtue of their intrinsic ionic character. Macroreticular strong base anion-exchange resins in the hydroxide form are particularly preferred in the practice of the present invention. Such resins are commercially available from or can be readily prepared from resins sold by Rohm and Haas Company under the registered trademark Amberlyst®, e.g., Amberlyst® A-26 and Amberlyst® A-27. Other suitable strong base anion-exchange resins are commercially available from others such as the Dow Chemical Company under the registered trademark DOWEX® 21K, 11 and MWA-1.

The resin matrix of weak base anion-exchange resins contains chemically bonded thereto a basic, nonionic functional group. The functional groups include primary, secondary, or tertiary amine groups. Of these, tertiary amine groups are preferred. These may be aliphatic, aromatic, heterocyclic or cycloalkane amine groups. They may also be diamine, triamine, or alkanolamine groups. The amines, for example, may include alpha, alpha'-dipyridyl, guanidine, and dicyanodiamidine groups. Other nitrogen-containing basic, non-ionic functional groups include nitrile, cyanate, isocyanate, thiocyanate, isothiocyanate, and isocyanide groups. Pyridine groups may also be employed. The present invention is not, however, limited to any particular class of weak base anion-exchange resins.

As weak base anion-exchange resins, the aminated, styrenedivinylbenzene copolymers, crosslinked with divinylbenzene to varying degrees in the molar range 1–40% of the monomer reacted, which also are commercially available from Rohm and Haas Company under the registered trademark Amberlyst®, are particularly useful. These resins can be prepared, for example, by the methods taught in U.S. Pat. No. 2,591,574 (McBurney, 1952) assigned to Rohn and Haas Company. Amberlyst® A-21, crosslinked using divinylbenzene is a useful resin for this invention because of its porous, insoluble bead structure. Amberlyst ® A-21 beads contain nitrogen in an amount of between about 4.2 and about 4.8 mequiv./gram resin, in the form of tertiary N,N-dimethylbenzylamine.

Weak base anion exchange resins are characterized by the fact that they possess essentially no ion exchange properties at pH levels greater than about pH 7 as above this pH they contain no ionic groups. As indicated above, they are composed of polymers containing primary, secondary, or tertiary amines, and the like. Further definition of strong and weak base ion exchange resins, along with a discussion of their preparation and properties, are described in F. Helfferich "Ion Exchange", McGraw Hill Book Co., New York, N.Y., 1962, pp. 16, 47-58, 78, 138-40, and in "Dowex-Ion Exchange", the Dow Chemical Co., Midland, Mich., 1958.

Strong acid cation-exchange resins also can be used to prepare the ionic ligand-functionalized resin used in connection with the present invention. Strong acid cation-exchange resins consist of polymers having sulfonic acid active ion-exchange sites. A suitable strong acid cation-exchange resin is available from Rohm and Haas Company under the registered trademark Amberlyst ® 15. Other suitable cation-exchange resins will be apparent to those skilled in the art.

As noted above, the resin employed should be insoluble in the rhodium-containing liquid. In the broad practice of the present invention, by "insoluble" we mean insoluble at temperatures below the decomposition temperature of the resin in the rhodium-containing liquid, e.g. polar and non-polar solvents such as water, alcohols, ketones, aldehydes, ethers, esters, acetic acid, in saturated, unsaturated or cyclic alphatic and aromatic hydrocarbons, and in the same hydrocarbons having substituents consisting of or containing oxygen, sulfur, nitrogen, or the halides.

The number of active ion-exchange sites per unit mass or unit volume of an ion-exchange resin suitable for preparing the ionic ligand-functionalized resin of the present invention may vary over a wide range and is not per se critical. The quantity of active sites available on a particular resin is quantified as the resin's "weight capacity", expressed as milliequivalents per gram (mEq/g). Generally, suitable resins will have a weight capacity of above about 0.5 mEq/g and preferably above about 1.0 mEq/g. For best results, substantially all of the active ion-exchange sites of the ion-exchange resin should be functionalized (i.e. substituted) with the ionic ligand.

When a strong base anion-exchange resin is contacted with the ionic organophosphorus ligand (e.g. an acidic or acidic salt derivative of an organophosphhous ligand) there is an actual interchange of the anionic ligand moiety for the anionic moiety associated with the active site of the resin, e.g. a hydroxyl radical. In the case of a weak base anion-exchange resin there is no interchange of anionic moieties, rather an acid-base reaction occurs between the acid form of the ionic ligand and the active site, e.g. the tertiary amine, on the weak base anion-exchange resin. In either case the resulting resin can be considered a "salt" with the anionic ligand moiety bonded to the resin by ionic forces, rather than covalent or coordinate forces. By contacting a strong acid cation-exchange resin with a basic derivative of an organophosphorus ligand, such as a dialkylamino-functionalized triphenylphosphine, an acid-base reaction occurs betwen the acid moiety on the resin and the basic dialkylamino group of the ligand. Procedures for preparing dialkylamino-substituted organophosphorus ligands are known in the art, see Zhmurova et al. Zh. Obshch. Khim., 36(7) pp 1248-54 (1966). The resulting resin also can be considered a salt with a cationic ligand moiety (quaternary ammonium) bonded to the anionic moiety (e.g. sulfonate) on the resin by ionic forces. It is to be understood that all of the above mechanisms and the like can be used in preparing the ionic ligand-functionalized resin employable in this invention.

It should be noted that commercial grade ion-exchange resin beads, such as the Amberlyst ® resins may be available in the halide, e.g., chloride, form or may contain halide impurities, e.g. chloride contaminates, which are known to poison (adversely affect) rhodium complex hydroformylation catalysts. Thus, it is preferred in the case of a hydroformylation-related process where the recovered rhodium is to be returned to the hydroformylation process that the ion-exchange resin employable herein be at least substantially free of halogen contaminates and more preferably essentially or entirely free from such halogen contaminates. Removal of such halogen contaminates, as well as any other undesirable contaminates, from such ion-exchange resins prior to their use may be readily accomplished by conventional ion-exchange and washing techniques that are well-known in the art.

As noted above, recovery of rhodium from polar or non-polar liquid solutions in accordance with the present invention can be surprisingly accomplished simply by contacting the liquid with the ionic ligand-functionalized resin. The quantity of ligand-functionalized ion-exchange resin relative to rhodium-containing liquid will depend upon the quantity of rhodium in the liquid and the binding strength of the ionically bound ligand for the dissolved rhodium. The quantity of ligand-functionalized ion-exchange resin need only be sufficient to reduce the rhodium concentration to the desired value. Based on a liquid standard having a rhodium concentration of about 10 ppm, an amount, by volume, of ionic liquid-functionalized resin of about 10 ml of resin per liter of liquid to be treated should be satisfactory for rhodium removal from a liquid. While rhodium can be removed from a liquid even in the presence of a large amount of free ligand, as is shown in the following examples, it is preferred that the amount of free ligand in the liquid to be treated be below about 10 mol equivalents of ligand per gram-atom of rhodium, more preferably below about 5 mol equivalents of ligand per gram-atom of rhodium and most preferably below about 2 mol equivalents ligand per gram-atom of rhodium. Best results are obtained if only trace amounts of free ligand, i.e. well below one mol of ligand per gram-atom of rhodium, are present in the liquid. Methods for reducing the level of ligand in a liquid are known.

The contact time between the resin and rhodium-containing liquid need only be sufficient to remove some of the rhodium from the liquid. The rhodium-containing liquid can be contacted with the ionic-ligand functionalized resin in either a batch or continuous (or semi-continuous) mode. When operating in a batch mode, the contact preferably involves agitation of a mixture of the rhodium-containing liquid and the resin for about 0.01 to 10 hours, more typically 0.1 to 5 hours, followed by any known separation technique, e.g. settling, centrifugation, filtration or the like. Preferably, the invention is practiced in a continuous mode by flowing the rhodium-containing liquid through one or more contained beds of the resin, e.g., a fixed bed, a moving bed or a fluidized bed, at a liquid flow rate ranging from about 0.1 to 100 bed volumes per hour, and more typically from 1 to 20 bed volumes per hour. The invention can employ any conventional apparatus designed for ion-exchange service, special designs are not required. Obviously, adequate contacting between the resin and liquid is important to obtain best results. As recognized by those skilled in this technology, the resin bed is used to remove rhodium from the liquid until the level (concentration) of rhodium in the treated liquid exiting the resin bed increases to above the desired value.

Rhodium subsequently can be removed from the loaded resin by contacting or eluting the resin with a polar or non-polar liquid containing solubilized organophosphorus ligand. Again, any polar or non-polar liquid can be used, subject only to compositional constraints referred to above. In a similar fashion, any of the wide variety of ionic and non-ionic organophosphorus ligands referred to above can be used for eluting rhodium from the loaded resin.

Illustrative non-ionic organophosphorus ligands that may be employable for eluting the loaded resin include, e.g., trialkylphosphines and phosphites, dialkylarylphosphines and phosphites, alkyldiarylphosphines and phosphites, triaralkylphosphines and phosphites, dicycloalkylarylphosphines and phosphites, cycloalkyldiarylphonphines and phosphites, tricycloalkylphosphines and phosphites, triarylphosphines and phosphites, alkyl and/or aryl bisphosphines and bisphosphine monoxides, diorganophosphites, organobisphosphites and polyphosphites, and the like. Mixtures of such ligands, as well as tertiary organophosphinite ligands, may also be employed if desired.

Preferred organophosphines include the tertiary organophosphines mentioned above, especially triphenylphosphines, propyldiphenylphosphines, n-butyldiphenylphosphines t-butyldiphenylphosphines, n-hexyldiphenylphosphines, cyclohexyldiphenylphosphines, dicyclohexylphenylphosphines, tricyclohexylphosphines, tribenzylphosphines, and the like. Preferred organophosphites include triarylphosphites e.g. triphenylphosphites as well as diorganophosphites such as disclosed e.g. in U.S. Pat. No. 4,717,775, organobisphosphites such as disclosed e.g. in U.S. Pat. No. 4,749,261 and organobis- and polyphosphites such as disclosed e.g. in U.S. Pat. No. 4,668,651.

A suitable ligand concentration for eluting rhodium from the loaded resin can be determined by routine experimentation. Generally, a solubilized ligand concentration in the eluent of about 0.1 to 2.0 mols per liter should be sufficient to remove rhodium from the bed, although higher ligand concentrations, e.g. up to 10 mols per liter and more, can be used and may be more advantageous in some circumstances. For example, rhodium can be freed from the resin by elution with a non-polar organic solution of a non-ionic organophosphine ligand (e.g. a triphenylphosphine or a cyclohexyldiphenylphosphine) or a non-polar organic solution of a non-ionic diorganophosphite to yield a non-polar organic solvent soluble rhodium complex suitable for use in known non-aqueous hydroformylation processes.

A particularly surprising feature of the present invention is that a solution of the same ionic organophosphorus ligand which is ionically bound to the resin can be used to remove (elute) complexed rhodium from the resin previously used to remove rhodium from the starting material. For example, rhodium loaded on an Amberlyst ® A-27 anionic-exchange resin functionalized with 3-(diphenylphosphino)- benzenesulfonic acid, i.e. triphenylphosphine monosulfonic acid (TPPMS) can be removed by eluting the resin with a 10 wt % solution of the sodium salt of this ligand, i.e. TPPMS-Na, in methanol (about 0.27 mol per liter). Tests have shown substantial rhodium removal from the resin bed with as little as 4 bed volumes of ligand solution. That one could use the same ligand to remove rhodium from the resin bed that was used to bind (complex) rhodium on the resin bed was completely unexpected. This process also regenerates the resin for direct reuse while simultaneously freeing the rhodium in a form which can be reintroduced directly into a hydroformylation system if so-desired.

Treatment pressures and temperatures for practicing the various aspects of the present invention are not narrowly critical to the performance of the invention, and standard (ambient) conditions can be used. The pressure is limited only by the physical strength of the resin. The temperature at any particular pressure should be such that the liquids remain in the liquid state. The temperature preferably is kept relatively low to minimize resin degradation, for example from about 0° C. to about 120° C.

EXAMPLES

The following examples are illustrative of the present invention and are not regarded as limiting. It should be understood that all of the parts, percentages, and proportions referred to herein and in the appended claims are by weight unless otherwise indicated. Also, the rhodium analysis are done by atomic absorption spectroscopy (AAS), unless otherwise indicated.

EXAMPLE A

Preparation of Triphenylphosphine Monosulfonic Acid (TPPMS) Bound A nion-Exchange Resin TPPMS (3-(diphenylphosphino)- benzenesulfonic acid) was bound to Amberlyst A-27 ion exchange resin for use in recovering trace rhodium from the product of a hydroformylation reaction wherein rhodium-containing catalyst was utilized.

Amberlyst A-27 first was converted serially from its chloride form to its bicarbonate form, then to its hydroxyl form. Solutions of sodium bicarbonate ($NaHCO_3$) and sodium hydroxide (coustic) were each prepared by adding 180 grams of the respective compound to 1800 milliliters of deionized water. One thousand eight hundred milliliters of 10 percent (w/v) sodium bicarbonate solution was passed through a column containing 90 milliliters of A-27 resin at a rate of 4 bed volumes per hour. The column then was washed with 450 milliliters of deionized water. The 10 percent (w/v) caustic solution (1800 milliliters) then was passed over the sodium bicarbonate-treated resin also at a rate of about 4 bed volumes per hour. The thus-converted resin in the hydroxyl form was rinsed with deionized water until the effluent had a neutral pH.

An aqueous solution of TPPMS (free acid form) was prepared by dissolving 35 grams of triphenylphosphine sodium monosulfonate (TPPMS-Na) in 665 grams deionized water. This solution was heated to facilitate dissolution, then, cooled, and filtered. The filtered solution was passed over 100 grams of Amberlite IRN-77 cation-exchange resin to convert the salt (TPPMS-Na)

to its free-acid form (TPPMS). The resin bed was washed with 1 bed volume of deionized water. The effluent, including the wash water, was collected, yielding 1,000 milliliters of acid TPPMS solution. The concentration of this acid TPPMS solution was determined by titration with 0.05N aqueous sodium hydroxide solution to have a normality of 0.099.

This TPPMS solution was eluted under ambient conditions over the A-27 resin (hydroxyl form) loaded in a 2 centimeter diameter and 50 centimeter length glass column. The concentration of the eluent recovered from the column was determined by titration to be 0.075N. To ensure that the resin was completed loaded with the TPPMS, the once-treated resin again was contacted with the TPPMS solution. The concentration of this second TPPMS eluent solution also was determined to be 0.075N after the second elution. The unchanged solution concentration indicated that the resin was fully loaded. The resin having TPPMS ionically bonded thereto then was washed with isopropanol. This resin subsequently was used to remove rhodium from various solutions and is identified in the following examples as Resin A.

EXAMPLE B

Preparation of Ionic Ligand-Functionalized Resin By Direct Ion Exchange of TPPMS-Na with Anion-Exchange Resin One hundred milliliters of Amberlyst A-27 resin (chloride form) was packed into a 2 centimeter diameter by 50 centimeter glass column. The resin was washed with 2 liters of 10 percent sodium bicarbonate solution solution to convert the resin to its bicarbonate form. The column then was washed with 200 milliliters of deionized water.

An aqueous solution of TPPMS-Na having a concentration of about 6.16 weight percent (determined by HPLC) was eluted under ambient conditions over the bicarbonate form of A-27 resin in the column. Six hundred milliliters of solution were passed over the resin at a rate of about 4 bed volumes per hour. After the first elution, the TPPMS-Na concentration had been reduced to about 4.04 weight percent. The so-prepared TPPMS-loaded resin was recovered for subsequent use and is identified in the following examples as Resin B.

EXAMPLE C

Preparation of Ionic Ligand Functionalized Resin with Ionically bound DIPHOS-MS

A method similar to that described in Example A was used to prepare a resin to which DIPHOS-MS (bisdiphenylphosphinoethane monosulfonic acid) was bonded ionically. In a ⅜ inch diameter by 50 centimeter stainless steel column, Amberlyst A-27 was modified to the hydroxyl form using the procedure as described in Example A. An aqueous solution of DIPHOS-MS then was passed under ambient conditions over this hydroxyl form of the resin in the column. Saturation of the resin with DIPHOS-MS was verified by titration. The so-prepared resin is identified in the following examples as Resin C.

EXAMPLE D

Preparation of Ionic Ligand Functionalized Resin with Ionically-Bound Ligand

Amberlite cation-exchange resin (about 109 grams) was contacted with 27.3 grams of the sodium salt of triphenylphosphine monosulfonic acid (TPPMS-Na) supplied as a 5% by wt. aqueous solution to convert the salt to its free-acid form (TPPMS). A column was loaded with about 20 grams of Amberlyst A-27 resin (chloride form) and washed with 300 mls of methanol and 300 mls of distilled water. The TPPMS solution then was flowed under ambient conditions through the A-27 resin column to prepare an ionic ligand-functionalized resin. Unbound ligand was removed from the resin by washing with isopropanol. The resin is identified in the following examples as Resin D.

EXAMPLE 1

Resins A and C were utilized to remove rhodium from the aldehyde (tridecanal) product stream recovered from a hydroformylation process as described in copending application Ser. No. 218,911 filed on Jul. 14, 1988 in which a rhodium-containing catalyst was utilized. The tridecanal aldehyde product also contained dodecene, water, a small amount of N-methylpyrrolidione and a variety of hydrofomylation by-products at very low concentrations. Table 1 below summarizes results achieved at various tridecanal flow rates, expressed in bed volumes per hour. The rhodium concentrations are expressed in parts per billion. The quantity of resin reported in Table 1 was packed into a ⅜ inch diameter by 50 centimeter stainless steel column through which the tridecanal stream was flowed. The percent recovery of rhodium on the resin from the solution is calculated based on the detection limit of the analytical equipment and thus represents a minimum value, rather than an actual value. The actual recovery probably was much higher.

TABLE 1

| Trace Rhodium Removal from Tridecanal | | | | | |
|---|---|---|---|---|---|
| Sample | Resin | Resin Quantity (g) | Aldehyde Flow Rate | Conc. $Rh_{In}$ (ppb) | Conc. $Rh_{Out}$ (ppb) | % Recovery (Minimum) |
| A | A | 16.7 | 2 | 110 | LL | 82 |
| B1 | A | 16.7 | 4 | 112 | LL | 82 |
| B2 | A | 16.7 | 4 | 87 | LL | 77 |
| C | A | 16.7 | 8 | 117 | LL | 83 |
| D | A | 16.7 | 12 | 103 | LL | 81 |
| E | C | 14.7 | 4 | 95 | LL | 79 |
| F | C | 14.7 | 12 | 93 | LL | 78 |

LL = actual Rh level undetectable, but was less than the lower limit of sensitivity of the AAS analyses, i.e., less than about 20 ppb.

EXAMPLE 2

This example illustrates the use of an ionic-ligand functionalized resin to remove rhodium from a hydroformylation catalyst solution and the subsequent use of another ligand solution to remove rhodium from the resin bed loaded with rhodium. Resin B was washed with deionized water, then contacted with 500 milliliters of 10 percent aqueous TPPMS-Na solution and again washed with deionized water and methanol. A 15.34 gram portion of this anionic ligand-functionalized resin was packed into a stainless steel column having a diameter of ⅜ inch and a length of 50 centimeters. A methanol solution containing 300 ppm rhodium (introduced as tetrarhodium dodecacarbonyl ($Rh_4(CO)_{12}$)) and 2 mol equivalents of TPPMS-Na was prepared. One hundred grams (126 milliliters) of this solution was recirculated over the Resin B bed in the column at a rate of about 1 ml per minute. After recirculation, the concentration of rhodium in the solution had been reduced to 4.4 ppm indicating substantial removal of rhodium from the solution (about 98% recovery).

The thus-treated resin column containing the bound rhodium then was washed with 100 grams of a 10 weight percent solution of TPPMS-Na in methanol to remove the bound rhodium from the resin. The rhodium concentration of the eluent was monitored by analyzing sequential fractions of the eluent to determine the rhodium removal from the resin by the TPPMS-Na solution. The results are summarized below in Table 2. The rhodium concentration of the cumulative washings (eluent) also was analyzed and determined to be 208 ppm.

TABLE 2

Recovery of Rh from Resin

| Sample | Bed Volumes | Rh. ppm |
|---|---|---|
| 1 | 1 | 942 |
| 2 | 2 | 267 |
| 3 | 3 | 88 |
| 4 | 4 | 40 |
| 5 | 5 | 27 |
| 6 | 5.6 | 21 |

To illustrate the ability of the resin to be used repeatedly, 126 milliliters (100 grams) of additional rhodium-containing solution (prepared in the same manner as above and containing 300 ppm rhodium) again was passed over the same resin. At the end of rhodium loading, the effluent had a concentration of 10 ppm rhodium, demonstrating substantial rhodium removal from the solution by the ligand-functionalized resin. Then, the rhodium-containing resin was washed with an additional 100 grams of 10 percent by weight TPPMS-Na methanol solution. The cumulative washings (eluent) had a rhodium concentration of 280 ppm, demonstrating substantial removal of rhodium from the resin bed by the ligand solution.

EXAMPLES 3 AND 4

The following examples also illustrate the ability of the ligand-functionalized resins of the present invention, prepared as described herein, to remove rhodium from solutions which contain free triphenylphosphine (TPP) ligand, in accordance with the method of the invention. After having previously been used as described in Example 1, the column containing Resin C was used to remove rhodium from spent hydroformylation catalyst. The spent hydroformylation catalyst was obtained from a process used to hydroformylate propylene to butyraldehyde using a rhodium- TPP complex catalyst and prior to treatment the light fraction had been stripped so that the recovered catalyst solution contained about 14 wt. % butyraldehyde, 18 wt. % triphenylphosphine (TPP) and the balance hydroformylation heavies. As the catalyst solution was eluted through the resin, periodic samples were taken to determine the concentration of rhodium in the eluent. Table 3 below summarizes the concentration of rhodium in sequential samples of the eluent as a function of total volume of solution passed through the resin. The solution was passed through the resin bed at a rate of 4 bed volumes per hour (sample Example 3).

Also summarized in Table 3 are the results of rhodium recovery from a fresh catalyst solution. The catalyst solution comprised a 10 percent solution of triphenylphosphine in Texanol® (Eastman brand 2,2,4-trimethyl-1,3-pentanediol monoisobutyrate) with 200 ppm rhodium (i.e., 5 grams triphenylphosphine in 45 grams Texanol with 0.0253 grams rhodium carbonyl acetyl acetonate). Before passing the catalyst solution through the resin, the catalyst was activated under hydroformylation conditions using equal molar parts of hydrogen, CO, and propylene, 60 psig reaction pressure and a temperature of 100° C. for 30 minutes. Sixteen grams of Resin A were placed into a column, and the fresh catalyst solution was passed through the bed at a rate of about 4 bed volumes per hour (sample Example 4).

TABLE 3

Rhodium Removal from Ligand-Containing Solutions

| Sample | Cummulative Total. ml Sample passed | Rh in eluent. ppm |
|---|---|---|
| Example 3 | 0 | 621 |
|  | 15 | 163 |
|  | 27 | 238 |
|  | 39 | 328 |
|  | 51 | 386 |
| Example 4 | 0 | 187 |
|  | 9 | 5 |
|  | 17 | 25 |
|  | 25 | 43 |
|  | 33 | 63 |
|  | 41 | 80 |
|  | 44 | 83 |

This data illustrates the removal of rhodium from catalyst solutions containing substantial levels of free ligand.

EXAMPLE 5

0.935 liters of a tridecanal aldehyde solution initially containing about 55 ppm of rhodium and about 0.2% TPPMS-Na ligand was continuously recirculated at a flow rate of 1.7 milliliters per minute through a 10 inch long and 0.5 inch diameter column packed with 22.4 grams of Amberlyst® A-27 anionic exchange resin functionalized with TPPMS ligand (Resin D). Samples of the recirculating flow were periodically withdrawn at a location just prior to the bed entry and were analyzed for rhodium concentration (ppm), weight percent TPPMS-Na ligand and weight percent TPPMS-Na oxide. The results are presented in Table 4. After sample Number 7 was drawn, the resin bed was replaced with new resin. A final rhodium concentration of 0.094 ppm was obtained, which corresponds to a total rhodium recovery of 99.8%.

TABLE 4

| Sample No. | Rhodium (ppm) | TPPMS-Na (ppm) | TPPMS-Na Oxide (ppm) |
|---|---|---|---|
| 1 | — | 0.060 | 0.071 |
| 2 | 53.6 | 0.357 | 0.075 |
| 3 | 56.8 | 0.283 | 0.083 |
| 4 | 27.8 | 0.299 | 0.079 |
| 5 | 16.1 | 0.305 | 0.070 |
| 6 | 13.1 | 0.154 | 0.372 |
| 7 | 10.6 | 0.062 | 0.402 |
| 8 | 10.2 | 0.001 | 0.210 |
| 9 | 4.79 | 0.296 | 0.133 |
| 10 | 0.194 | 0.239 | 0.112 |
| 11 | 0.161 | 0.210 | 0.293 |
| 12 | 0.094 | 0.269 | 0.113 |

EXAMPLE 6

200 milliliters of a solution containing 50 ppm of rhodium (supplied as rhodium carbonyl acetyl acetonate) and 1 wt % triphenylphosphine (TPP) in Texanol® solvent was recirculated over a 10 inch long and ½ inch diameter column containing the same ionic ligand-functionalized resin used in Example 5. (Resin D) After 17 hours of recirculation, the rhodium concentration in the solution decreased to 3 ppm, which corresponds to about a 94% rhodium recovery.

EXAMPLE 7

This example illustrates the removal of rhodium from the loaded bed produced in Example 6 using a triphenylphosphine (TPP) solution. Upon increasing the TPP ligand concentration of the recirculating Texanol® solution of Example 6 containing 3 ppm rhodium to about 10 wt. %, and after about 26 hours of additional circulation over the same resin loaded with rhodium previously in Example 6, rhodium was eluted from the resin so that the rhodium concentration in the recirculating solution increased from 3 ppm to 10.2 ppm.

EXAMPLE 8

Recirculation of 400 ml of a tridecanal solution was established through a 10 inch long and ½ inch diameter column loaded with 50 ml of an ionic ligand-functionalized resin (Resin D). The recirculation flow was set at about 1.5 ml/min. To simulate a process for continuously removing rhodium, an N-methylpyrrolidione solution containing 175 ppm of rhodium and 2 mol equivalents of TPPMS-Na per gram-atom of rhodium was periodically infused into the recirculating aldehyde stream. The rhodium concentration of the stream entering and exiting the resin bed were analyzed periodically and the results are reported in Table 5.

TABLE 5

| Day | Cumulative Vol. of Infused Rh Solution (ml) | $Rh_{(in)}$ (ppb) | $Rh_{(out)}$ (ppb) | Rh Removal per pass (%) | Total Rh Removal (%) |
|---|---|---|---|---|---|
| 5 | 20 | 1115 | 271 | 75 | 87.5 |
| 8 | 35 | 1494 | 332 | 78 | 90.0 |
| 15 | 63 | 964 | 656 | 32 | 96 |
| 19 | 78 | 1180 | 870 | 26 | 96 |
| 29 | 103 | 1953 | 1782 | 9 | 96 |

Thus, while certain specific embodiments of the invention have been described with particularity herein, it will be recognized that various modifications thereof will occur to those skilled in the art and it is to be understood that such modification and variations are to be included within the purview of this application and the spirit and scope of the appended claims.

We claim:

1. A method for recovering Group VIII transition metal from a transition metal-containing liquid which comprises
   (i) contacting said transition metal-containing liquid with an ion-exchange resin wherein said resin has a first organophosphorus ligand bonded ionically thereto, to cause transition metal to be removed from the liquid and bound to the resin, and
   (ii) thereafter contacting said resin with a liquid containing a sufficient quantity of a second organophosphorus ligand to remove transition metal from the resin.

2. The method of claim 1 wherein said transition metal is rhodium.

3. The method of claim 2 wherein said rhodium-containing liquid comprises an aldehyde product of a hydroformylation process containing 2 ppm or less of rhodium.

4. The method of claim 1 wherein said ion-exchange resin is an anionic-exchange resin having an organophosphorus ligand bonded ionically thereto.

5. The method of claim 4 wherein said anionic exchange resin is a macroreticular, strong base anionic-exchange resin.

6. The method of claim 1 wherein said first and second organophosphorus ligands are the same.

7. The method of claim 6 wherein said second ligand-containing liquid is a polar liquid.

8. The method of claim 7 wherein said polar liquid is methanol.

9. The method of claim 6 wherein said organophosphorus ligands are ionic organophosphines.

10. The method of claim 9 wherein said ionic organophosphines are selected from compounds having the general formulae (1) and (2):

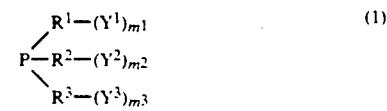

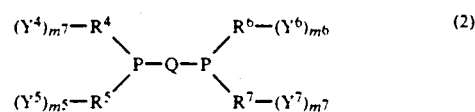

wherein $R^1$, $R^2$ and $R^3$ of formula (1) and $R^4$, $R^5$, $R^6$ and $R^7$ of formula (2) each individually represent a hydrocarbon radical containing from 1 to 30 carbon atoms selected from the group consisting of alkyl, aryl, alkaryl, aralkyl, and cycloalkyl radicals, where Q in formula (2) represents a divalent organic bridging group and where $Y^1$, $Y^2$ and $Y^3$ of formula (1) and $Y^4$, $Y^5$, $Y^6$ and $Y^7$ of formula (2) are substituted on the hydrocarbon radical and each individually represents an ionic radical of overall neutral charge selected from the group consisting of;

—$SO_3M$ wherein M represents inorganic or organic cationic atoms or radicals,

—$PO_3M$ wherein M represents inorganic or organic cationic atoms or radicals,

—$NR_3X'$ wherein R represents a hydrocarbon radical containing from 1 to 30 carbon atoms selected from the class consisting of alkyl, aryl, alkaryl, aralkyl, and cycloakyl radicals, and X' represents inorganic or organic anionic atoms or radicals, —$CO_2M$ wherein M represents inorganic or organic cationic atoms or radicals, wherein $m^1$, $m^2$ and $m^3$ of formula (1) and $m^4$, $m^5$, $m^6$ and $m^7$ of formula (2) are integers which can be the same or different and which can range from 0 to 5, and wherein at least one of $m_1$, $m_2$ and $m_3$ in formula (1) and at least one of $m_4$, $m_5$, $m_6$ and $m_7$ in formula (2) is equal to or greater than 1.

11. The method of claim 6 wherein said organophosphorus ligands are an ionic organophosphites.

12. The method of claim 11 wherein said ionic organophosphites are selected from the group consisting of (i) poly-phosphites having the formula substituted on an aryl moiety of Ar, D or T.

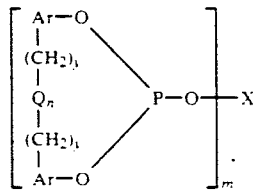

(I)

wherein each Ar group represents an identical or different aryl radical; wherein X represents an m-valent hydrocarbon radical selected from the group consisting of alkylene, alkylene-oxy-alkylene, aryl, and aryl-$(CH_2)_y$—$(Q)_n$—$(CH_2)_y$-aryl; wherein each y individually has a value of 0 or 1; wherein each Q individually represents a divalent bridging group selected from the class consisting of —$CR^1R^2$—, —O—, —S—, —$NR^3$—, —$SiR^4R^5$—, and —CO—, wherein $R^1$ and $R^2$ each individually represents a radical selected from the group consisting of hydrogen, alkyl of 1 to 12 carbon atoms, phenyl, tolyl and anisyl, wherein $R^3$, $R^4$, and $R^5$ each individually represents —H or —$CH_3$; wherein each n individually has a value of 0 to 1; wherein m has a value of 2 to 6; and wherein the poly-phosphites of formula (I) contain at least one ionic radical of overall neutral charge selected from the group consisting of —$SO_3M$ wherein M represents inorganic or organic cationic atoms or radicals, substituted on an aryl moiety of Ar, D or T, —$PO_3M$ wherein M represents inorganic or organic cationic atoms or radicals, —$NR_3X'$ wherein R represents a hydrocarbon radical containing from 1 to 30 carbon atoms selected from the class consisting of alkyl, aryl, alkaryl, aralkyl, and cycloakyl radicals, and X' represents inorganic or organic anionic atoms or radicals, —$CO_2M$ wherein M represents inorganic or organic cationic atoms or radicals, substituted on an aryl moiety of Ar or X;

(ii) diorganophosphites having the formula

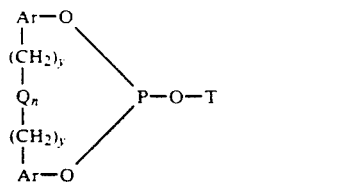

(II)

wherein T represents a monovalent hydrocarbon radical; wherein Ar, Q, n, and y are as defined above; and wherein the diorganophosphites of formula (II) contain at least one ionic radical of overall neutral charge selected from the group consisting of —$SO_3M$ wherein M represents inorganic or organic cationic atoms or radicals, —$PO_3M$ wherein M represents inorganic or organic cationic atoms or radicals, —$NR_3X'$ wherein R represents a hydrocarbon radical containing from 1 to 30 carbon atoms selected from the class consisting of alkyl, aryl, alkaryl, aralkyl, and cycloakyl radicals, and X' represents inorganic or organic anionic atoms or radicals, —$CO_2M$ wherein M represents inorganic or organic cationic atoms or radicals, substituted on an aryl moiety of Ar or T; and (iii) open-ended bis-phosphites having the formula

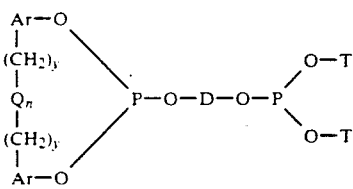

(III)

wherein D represents a divalent bridging group selected from the group consisting of alkylene, alkylene-oxy-alkylene, aryl, and aryl-$(CH_2)_y$—$Q_n$—$(CH_2)_y$-aryl; wherein Ar, Q, n, y, and T are as defined above and each T may be identical or different; and wherein the bis-phosphites of formula (III) contain at least one ionic radical of overall neutral charge selected from the group consisting of —$SO_3M$ wherein M represents inorganic or organic cationic atoms or radicals, —$PO_3M$ wherein M represents inorganic or organic cationic atoms or radicals, —$NR_3X'$ wherein R represents a hydrocarbon radical containing from 1 to 30 carbon atoms selected from the class consisting of alkyl, aryl, alkaryl, aralkyl, and cycloakyl radicals, and X' represents inorganic or organic anionic atoms or radicals, —$CO_2M$ wherein M represents inorganic or organic cationic atoms or radicals, substituted on an aryl moiety of Ar, D or T.

13. An ion-exchange resin having an organophosphorus ligand bonded ionically thereto.

14. The ion-exchange resin of claim 13 wherein said organophosphorus ligand is an ionic organophosphine.

15. The ion-exchange resin of claim 13 wherein said organophosphorus ligand is an ionic organophosphite.

16. A method for recovering rhodium from an aldehyde product of a hydroformylation process, wherein said aldehyde product contains 2 ppm or less of rhodium, which comprises
(i) contacting said aldehyde product with an ion-exchange resin, wherein said resin has an ionic organophosphorus ligand bonded ionically thereto, to cause rhodium to be removed from the liquid and bound to the resin, and
(ii) thereafter contacting said resin with a liquid containing a sufficient quantity of said ionic organophosphorus ligand to remove rhodium from the resin and regenerate the resin for reuse.

17. The method of claim 16 wherein the ionic organophosphorus ligand bonded ionically to said resin and the ionic organophosphorus ligand employed to remove the rhodium from the resin are the same.

* * * * *

UNITED STATES PATENT AND TRADEMARK OFFICE
CERTIFICATE OF CORRECTION

PATENT NO. : 5,114,473

DATED : May 19, 1992

INVENTOR(S) : Anthony E. Abatjoglou and David R. Bryant

It is certified that error appears in the above-identified patent and that said Letters Patent is hereby corrected as shown below:

Column 28, lines 67 and 68: the phrase "substituted on an aryl moiety of Ar, D or T." should be deleted.

Signed and Sealed this

First Day of March, 1994

Attest:

Attesting Officer

BRUCE LEHMAN

Commissioner of Patents and Trademarks